United States Patent [19]

Tomcufcik et al.

[11] Patent Number: 4,499,097

[45] Date of Patent: Feb. 12, 1985

[54] 2-(PYRIDYL)IMIDAZOLYL KETONES

[75] Inventors: Andrew S. Tomcufcik, Old Tappan, N.J.; Walter E. Meyer, Suffern; Nancy H. Eudy, Cornwall-on-Hudson, both of N.Y.

[73] Assignee: American Cyanamid Company, Stamford, Conn.

[21] Appl. No.: 473,939

[22] Filed: Mar. 10, 1983

[51] Int. Cl.³ .................. C07D 401/04; A61K 31/415
[52] U.S. Cl. ..................................... 514/341; 546/278
[58] Field of Search ......................... 546/278; 424/263

[56] References Cited

U.S. PATENT DOCUMENTS 3,929,807 12/1975 Fitzi ..................................... 546/278
4,125,530 11/1978 Baldwin et al. ..................... 546/278
4,281,005 7/1981 Baldwin .............................. 546/278

Primary Examiner—Jane T. Fan
Attorney, Agent, or Firm—Edward A. Conroy, Jr.

[57] ABSTRACT

This disclosure describes novel substituted 2-(pyridyl)imidazol-4-yl ketones and derivatives thereof which possess activity as hypotensive agents.

25 Claims, No Drawings

2-(PYRIDYL)IMIDAZOLYL KETONES

BRIEF SUMMARY OF THE INVENTION

This invention relates to new organic compounds and, more particularly, is concerned with novel substituted 2-(pyridyl)imidazol-4-yl ketones (I) and tautomers thereof (II) which may be represented by the following structural formulae:

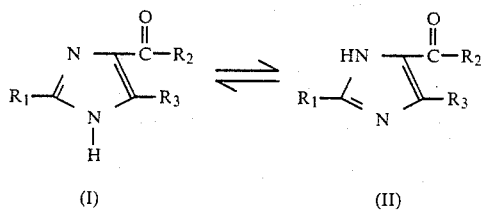

(I)     (II)

wherein $R_1$ is a substituted 2-pyridyl, 3-pyridyl or 4-pyridyl moiety of the formula:

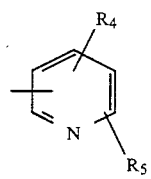

wherein $R_4$ and $R_5$ are each individually selected from the group consisting of hydrogen, chloro and methyl with the proviso that $R_4$ and $R_5$ may not both be chloro or methyl; $R_2$ is alkyl having from one to five carbon atoms, cycloalkyl having from three to six carbon atoms or phenyl; and $R_3$ is alkyl having from one to three carbon atoms. Suitable alkyl groups contemplated by the present invention are methyl, ethyl, n-propyl, isopropyl, n-butyl, isobutyl, sec-butyl, tert-butyl, n-amyl, isoamyl, 1-ethylpropyl, 1,2-dimethylpropyl, 1-methylbutyl, 2-methylbutyl, tert-amyl and neopentyl. Suitable cycloalkyl groups contemplated by the present invention are cyclopropyl, cyclobutyl, cyclopentyl and cyclohexyl.

The novel substituted 2-(pyridyl)imidazol-4-yl ketones (and tautomers thereof) of the present invention form carbonyl derivatives such as oximes, methoximes and semicarbazones. They also form pyridine-1-oxides and quaternary derivatives such as 1-alkylpyridinium halides and 1-(phenylalkyl)pyridinium halides. In this context; suitable alkyl groups are those having from one to three carbon atoms, suitable phenylalkyl groups are benzyl, α-phenethyl and β-phenethyl, whereas halide is exemplified by chloride, bromide and iodide.

DETAILED DESCRIPTION OF THE INVENTION

The novel compounds of the present invention are generally obtainable as colorless, white, tan or pale yellow crystalline solids having characteristic melting points and absorption spectra. They are generally soluble in many organic solvents such as lower alkanols, chloroform, tetrahydrofuran, N,N-dimethylformamide, ethyl acetate and the like, they are also soluble in acids and alkalis and certain of the compounds are soluble in water. The novel compounds of the present invention are relatively insoluble in non-polar organic solvents such as diethyl ether, hexane, benzene, toluene and the like.

Certain of the organic bases of the present invention form non-toxic acid-addition salts with a variety of pharmacologically acceptable organic and inorganic salt forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumaric, succinic, tartaric, acetic, benzoic, gluconic, ascorbic and the like. The acid-addition salts are also relatively insoluble in the aforesaid non-polar organic solvents but are appreciably soluble in water. For purposes of this invention, the free bases are equivalent to their non-toxic acid-addition salts.

The novel compounds of the present invention may be readily prepared as set forth in the following reaction scheme:

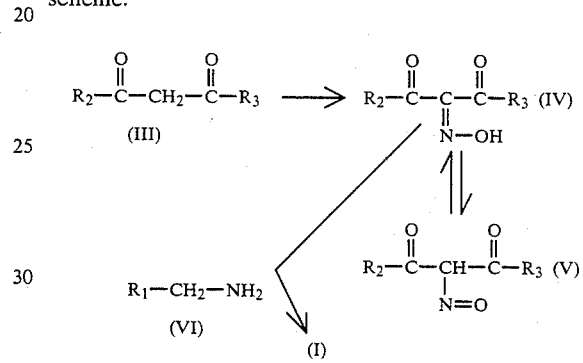

wherein $R_1$, $R_2$ and $R_3$ are as hereinbefore defined. In accordance with the above reaction scheme, an appropriately substituted 1,3-dione (III) is converted to the correspondng 2-oximino-1,3-dione (IV) and its tautomeric 2-nitroso-1,3-dione (V) by the procedures described in Beilstein, Vol. I, 807 (3rd ed.) and Ann. 325, 139 (L. Wolff). Condensation of the 2-oximino-1,3-dione (IV) with an appropriately substituted pyridylmethylamine (VI) provides the corresponding 2-(pyridyl)imidazol-4-yl ketones (I). This condensation is best carried out in an inert solvent such as acetonitrile, methyl cellosolve, pyridine, and the like at the reflux temperature thereof for 1-20 hours. The products (I) may be isolated by standard procedures and purified by crystallization from common solvents such as ethanol, acetonitrile, toluene and ethyl acetate or combinations of solvents such as ethyl acetate/hexane or ethyl acetate/diethyl ether.

The novel compounds of the present invention are physiologically active and therefore useful in the pharmaceutical field. In particular, these compounds possess anti-hypertensive activity at non-toxic doses and, as such, are useful as hypotensive agents. The hypotensive properties of the compounds of the present invention have been shown when orally administered to mammals, specifically warm-blooded animals as described below.

The novel compounds of the present invention were tested for anti-hypertensive activity in a procedure using spontaneously hypertensive rates (SHR) having an average mean arterial blood pressure of 170±1.5 mm. of mercury as follows. One male adult SHR (16–20 weeks old) weighing about 300 grams (Taconic Farms, Germantown, N.Y.) is dosed by gavage with the test compound at one to 100 mg/kg of body weight with 0.9% sodium chloride loading at 25 ml/kg of body weight at zero hour. A second identical dose is given at 24 hours without saline loading and the mean arterial blood pressure (MABP) of the conscious rat is measured directly by femoral artery puncture at 28 hours. A 2nd or 3rd SH rat may be needed depending on the results of the 1st rat [Chan, et al., Pharmacologist, 17, 253 (1975)]. Representative compounds of the present invention have been shown to possess anti-hypertensive activity when tested as described above and as set forth in Table I below.

TABLE I

| Compound | Dose mg./kg. | MABP mm. of Hg |
|---|---|---|
| 1-[5-Methyl-2-(3-pyridinyl)-1H—imidazol-4-yl]ethanone | 100 | 79 |
| [5-Methyl-2-(3-pyridinyl)-1H—imidazol-4-yl]phenylmethanone | 100 | 124 |
| 1-[5-Propyl-2-(3-pyridinyl)-1H—imidazol-4-yl]-1-butanone | 100 | 125 |
| 2-Methyl-1-[5-methyl-2-(3-pyridinyl)-1H—imidazol-4-yl]-1-propanone | 100 | 94 |
| 1-[5-Methyl-2-(3-pyridinyl)-1H—imidazol-4-yl]-1-butanone | 100 | 75 |
| 1-[5-Methyl-2-(3-pyridinyl)-1H—imidazol-4-yl]-1-pentanone | 100 | 112 |
| 2,2-Dimethyl-1-[5-methyl-2-(3-pyridinyl)-1H—imidazol-4-yl]-1-propanone | 100 | 117 |
| 1-[5-Methyl-2-(3-pyridinyl)-1H—imidazol-4-]-1-hexanone | 100 | 104 |
| 1-[5-Methyl-2-(3-pyridinyl)-1H—imidazol-4-yl]-1-propanone | 100 | 77 |
| 3-Methyl-1-[5-methyl-2-(3-pyridinyl)-1H—imidazol-4-yl]-1-butanone | 100 | 126 |
| 1-[5-Ethyl-2-(3-pyridinyl)-1H—imidazol-4-yl]-1-propanone | 100 | 89 |
| 2-Methyl-1-[5-methyl-2-(3-pyridinyl)-1H—imidazol-4-yl]-1-butanone | 100 | 88 |
| Cyclopropyl[5-methyl-2-(3-pyridinyl)-1H—imidazol-4-yl]methanone | 100 | 88 |
| Cyclohexyl[5-methyl-2-(3-pyridinyl)-1H—imidazol-4-yl]methanone | 100 | 129 |
| 1-[5-Ethyl-2-(3-pyridinyl)-1H—imidazol-4-yl]-2,2-dimethyl-1-propanone | 100 | 133 |
| 1-[5-Methyl-2-(pyridinyl)-1H—imidazol-1-yl]ethanone | 100 | 140 |
| 1-[2-(2-Chloro-6-methyl-3-pyridinyl)-5-methyl-1H—imidazol-4-yl]ethanone | 100 | 150 |
| 1-[5-Methyl-2-(4-pyridinyl)-1H—imidazol-4-yl]ethanone | 100 | 115 |
| 1-[2-(6-Chloro-3-pyridinyl)-5-methyl-1H—imidazol-4-yl]ethanone | 100 | 119 |
| 1-[5-Methyl-2-(3-methyl-4-pyridinyl)-1H—imidazol-4-yl]ethanone | 100 | 77 |
| 1-[5-Methyl-2-(3-pyridinyl)-1H—imidazol-4-yl]ethanone oxime | 100 | 74 |
| 1-[5-Methyl-2-(4-pyridinyl)-1H—imidazol-4-yl]ethanone oxime | 100 | 110 |
| 1-[5-Methyl-2-(3-methyl-4-pyridinyl)-1H—imidazol-4-yl]ethanone oxime hydrate | 100 | 82 |
| 1-[5-Methyl-2-(3-pyridinyl)-1H—imidazol-4-yl]ethanone-O—methyloxime | 100 | 108 |

The novel compounds of the present invention have been found to be highly useful for lowering elevated blood pressure in mammals when administered in amounts ranging from about 0.4 mg. to about 10.0 mg/kg of body weight per day. A preferred dosage regimen for optimum results would be from about 7.0 mg. to about 175 mg/dose. Such dosage units are employed that a total of from about 28 mg. to about 700 mg. of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as the intravenous route.

The compounds of the present invention may be administered as active components of compositions in unit dosage form such as tablets, pills, capsules, powders, granules, oral or parenteral solutions or suspensions and the like. For preparing solid compositions such as tablets, the active compound is mixed with conventional tableting ingredients such as starch, lactose, sucrose, sorbitol, talc, stearic acid, magnesium stearate, dicalcium phosphate, gums and functionally similar materials as pharmaceutical diluents or carriers. The tablets or pills can be laminated or otherwise compounded to provide a dosage form affording the advantage of prolonged or delayed action, or predetermined successive action of the enclosed medication. For example, the tablet or pill can comprise an inner and an outer dosage component, the latter being in the form of an envenlope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolymer together with known materials contributing to the enteric properties of the coating.

Compositions according to the present invention having the desired clarity, stability and adaptability for parenteral use are obtained by dissolving from 0.10% to 10% by weight of active compound in a vehicle consisting of a polyhydric aliphatic alcohol or mixtures thereof. Especially satisfactory are glycerin, propylene, glycol, and polyethylene glycols. The polyethylene glycols consist of a mixture of non-volatile, normally liquid, polyethylene glycoles which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

The novel compounds of the present invention are adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The liquid forms in which the compounds of the present invention may be incorporated for administration include aqueous solutions, suitably flavored syrups, aqueous or oil suspension, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitation inherent in the art of compounding such an active material for therapeutic use, as disclosed in detail in the specification, these being features of the present invention.

The invention will be described in greater detail in conjunction with the following specific examples.

EXAMPLE 1

1-[5-Methyl-2-(3-pyridinyl)-1H-imidazol-4-yl]ethanone

The compound 2,3,4-pentanetrione, 3-oxime, mp 73°–74° C. (from dichloromethane), was prepared from 2,4-pentanedione by the methods described in Beilstein, Vol I, 807, 3rd Ed., and by L. Wolff, Ann. 325, 139.

A mixture of 6.5 g (0.05 mole) of the preceding compound and 6.0 g (0.055 mole of 3-pyridylmethylamine in 125 ml of acetonitrile was stirred at the reflux temperature for 2½ hours. The reaction mixture was cooled at −10° C. to yield a precipitate. The precipitate was collected by filtration, washed with 25 ml of cold dichloromethane and air dried. The material was recrystallized from acetonitrile and dried to give 5.3 g of the desired product as a pale yellow solid, mp 198°–199° C.

EXAMPLE 2

1-[5-Methyl-2-(3-pyridinyl)-1H-imidazol-4-yl]-ethanone oxime

To a 20.0 g (0.0995 mole) amount of 1-[5-methyl-2-(3-pyridinyl)-1H-imidazol-4-yl]ethanone (prepared as described in Example 1) dissolved in 500 ml of boiling water were added 15.0 g (0.183 mole) of sodium acetate and 10.0 g (0.144 mole) of hydroxylamine hydrochloride. The mixture was stirred and heated for 4 hours, then cooled to room temperature. The resulting precipitate was collected by filtration and when dried at 140°–160° C. for 24 hours gave 20.3 g of the desired product as a white solid, mp 215°–216° C.

EXAMPLE 3

2-[1-[5-Methyl-2-(3-pyridinyl)-1H-imidazol-4-yl]-ethylidene]hydrazinecarboxamide A 4.0 g (0.02 mole) amount of 1-[5-methyl-2-(3-pyridinyl)-1H-imidazol-4-yl]ethanone was dissolved in 200 ml of boiling water containing 6.0 g (0.073 mole) of sodium acetate. The solution was clarified by treatment with activated charcoal then filtered. A 4.0 g (0.036 mole) amount of semicarbazide hydrochloride was dissolved in 50 ml of water and clarified as above. This solution was added to the reaction mixture filtrate above and boiled gently for 10 minutes. The mixture was cooled to room temperature. The precipitate was collected by filtration, washed with water, then dried and gave 2.7 g of the product of the Example as a yellow solid, mp 220°–225° C. (dec.).

EXAMPLE 4

1-[5-Methyl-2-(3-pyridinyl)-1H-imidazol-4-yl]-ethanone O-methyloxime

A 4.0 g (0.002 mole) amount of 1-[5-methyl-2-(3-pyridinyl)-1H-imidazol-4-yl]ethanone was dissolved in 150 ml of boiling water. The solution was clarified by treatment with activated charcoal, then filtered. The filtrate was added to a mixture of 2.0 g (0.025 mole) of O-methylhydroxylamine hydrochloride, 2.0 g (0.025 mole) of sodium acetate and 10 ml of water. This mixture was stirred and heated on a steam bath for 16 hours. The hot solution was clarified with activated charcoal and filtered. A 150 ml volume of water was added to the filtrate which had developed a heavy precipitate. The mixture was stirred and heated to boiling and ethanol was added in small portions to effect solution. The hot solution was clarified with activated charcoal and filtered. The filtrate was cooled at 5° C. with formation of a precipitate. The solid was collected by filtration, washed with cold water and dried and gave 1.7 g of the desired product as a white solid, mp 203°–205° C.

EXAMPLE 5

1-[5-Methyl-2-(3-pyridinyl)-1H-imidazol-4-yl]-ethanone pyridine-1-oxide

A 5.0 g (0.025 mole) amount of 1-[5-methyl-2-(3-pyridinyl)-1H-imidazol-4-yl]ethanone was dissolved in 500 ml of dichloromethane and 250 ml of chloroform. Then 5.0 g (0.025 mole) of m-chloroperbenzoic acid (86–90%) was added. The solution was stirred at room temperature and after one hour a precipitate began to form. Stirring was continued for 23 hours. The precipitate was collected by filtration, washed with 50 ml of dichloromethane and air dried. The precipitate was recrystallized from ethanol and gave 1.3 g of the desired product as a white solid, mp 288°–292° C. (dec.).

EXAMPLE 6

3-(4-Acetyl-5-methyl-1H-imidazol-2-yl)-1-methyl-pyridinium iodide

A 3.0 g (0.015 mole) amount of 1-[5-methyl-2-(3-pyridinyl)-1H-imidazol-4-yl]ethanone in 300 ml of acetone was treated with 3.0 ml of methyl iodide. The reaction mixture was allowed to stand at room temperature for 24 hours. The precipitate formed was collected by filtration and was washed with 50 ml each of acetone and ether then was dried in vacuo at 60° C. to yield 1.9 g of the desired product as a yellow solid, mp 258°–260° C. (dec.).

EXAMPLE 7

3-(4-Acetyl-5-methyl-1H-imidazol-2-yl)-1-(phenylmethyl)pyridinium chloride

A mixture of 10.0 g (0.05 mole) of 1-[5-methyl-2-(3-pyridinyl)-1H-imidazol-4-yl]ethanone, 13 ml (0.1+ mole) of benzyl chloride, 10 ml (0.05+ mole) of N,N-diisopropylethylamine and 250 ml of dioxane was stirred at reflux for 18 hours. The resulting precipitate was collected by filtration of the hot mixture, washed free of color with tetrahydrofuran, then dried in vacuo at 100° C. and gave 12.2 g of the desired product as a yellow solid, mp 230°–232° C.

EXAMPLES 8–21

The following 2-(3-pyridinyl)imidazole compounds listed in Table II were prepared from the corresponding oximes which in turn were prepared from the corresponding diones as described by literature methods and procedures as described in Example 1, refluxing from 1–20 hours.

EXAMPLE 22

1-[5-Methyl-2-(2-pyridinyl)-1H-imidazol-4-yl]ethanone

A mixture of 6.5 g (0.05 mole) of 2,3,4-pentanetrione 3-oxime and 6.0 g (0.055 mole) of 2-pyridylmethylamine in 125 ml of acetonitrile was stirred and refluxed as described in Example 1. Cooling at −10° C. gave a precipitate which was recrystallized from acetonitrile to give 3.6 g of the product of the Example as a yellow solid, mp 145°–147° C.

EXAMPLE 23

1-[2-(2-Chloro-6-methyl-3-pyridinyl)-5-methyl-1H-imidazol-4-yl]ethanone

A mixture of 0.7 g of 2,3,4-pentanetrione 3-oxime and 0.9 g of 2-chloro-6-methyl-3-pyridylmethylamine in 50 ml of acetonitrile was stirred at the reflux temperature for 4 hours. The reaction mixture was evaporated in vacuo to give an oil. The oil was boiled in 50 ml. of water, treated with activated charcoal and filtered. The filtrate was cooled at 5° C. to yield a precipitate. The precipitate was collected, washed with cold water and dried to give 0.25 g of the product of the Example as a white solid, mp 156°–158° C.

TABLE II

| Ex. | Starting Dione | Intermediate Oxime | Reflux Time In Hours | $R_2$ | $R_3$ | MP° C. | Crystallization Solvent |
|---|---|---|---|---|---|---|---|
| 8 | 1-Phenyl-1,3-butanedione | 1-Phenyl-1,2,3-butanetrione, 2-oxime | 5 |  | —$CH_3$ | 175–180 | Toluene |
| 9 | 4,6-Nonanedione | 4,5,6-Nonanetrione 5-oxime | 2.5 | —$C_3H_7n$- | —$C_3H_7n$ | 170–172 | Ethyl Acetate |
| 10 | 5-Methyl-2,4-hexanedione | 5-Methyl-2,3,4-hexanetrione 3-oxime | 18 | —$CH(CH_3)_2$ | —$CH_3$ | 153–154 | Ethyl Acetate/Hexane |
| 11 | 2,4-Heptanedione | 2,3,4-Heptanetrione, 3-oxime | 16 | —$C_3H_7n$- | —$CH_3$ | 151–153 | Ethyl Acetate/Hexane |
| 12 | 2,4-Octanedione | 2,3,4-Octanetrione 3-oxime | 3 | —$C_4H_9n$- | —$CH_3$ | 106–107 | Ethyl Acetate/Hexane |
| 13 | 5,5-Dimethyl-2,4-hexanedione | 5,5-Dimethyl-2,3,4-hexanetrione 3-oxime | 18 | —$C(CH_3)_3$ | —$CH_3$ | 178–179 | Ethyl Acetate/Ether/Hexane |
| 14 | 2,4-Nonanedione | 2,3,4-Nonanetrione 3-oxime | 16 | —$C_5H_{11}n$- | —$CH_3$ | 101–103 | Ethyl Acetate |
| 15 | 2,4-Hexanedione | 2,3,4-Hexantrione 3-oxime | 5 | —$C_2H_5$ | —$CH_3$ | 163–165 | Ethyl Acetate |
| 16 | 5-Methyl-2,4-heptanedione | 6-Methyl-2,3,4-heptanetrione 3-oxime | 5.5 | —$CH_2CH(CH_3)_2$ | —$CH_3$ | 139–140 | Ethyl Acetate |
| 17 | 3,5-Heptanedione | 3,4,5-Heptantrione 4-oxime | 3 | —$C_2H_5$ | —$C_2H_5$ | 152–153 | Water |
| 18 | 5-Methyl-2,4-heptanedione | 5-Methyl-2,3,4-heptanetrione 3-oxime | 7 | —$CH(CH_3)C_2H_5$ | —$CH_3$ | Semi-solid | Water |
| 19 | 1-Cyclopropyl-1,3-butanedione | 1-Cyclopropyl-1,2,3-butanetrione 2-oxime | 5.5 |  | —$CH_3$ | 216–217 | Acetonitrile/Isopropanol |
| 20 | 1-Cyclohexyl-1,3-butanedione | 1-Cyclohexyl-1,2,3-butanetrione 2-oxime | 7 |  | —$CH_3$ | 215–216 | Acetonitrile/Isopropanol |
| 21 | 7,7-Dimethyl-3,5-octanedione | 7,7-Dimethyl-3,4,5-octanetrione 4-oxime | 20 | —$C(CH_3)_3$ | —$C_2H_5$ | 201–202 | Methanol |

EXAMPLE 24

1-[5-Methyl-2-(4-pyridinyl)-1H-imidazol-4-yl]ethanone

A mixture of 6.5 g (0.05 mole) of 2,3,4-pentanetrione 3-oxime and 6.0 g (0.055mole) of 4-pyridylmethylamine in 75 ml of N,N-dimethylformamide was stirred at the reflux temperature for 4 hours. The solvent was removed in vacuo and 100 ml of acetonitrile was added to the residual oil. The mixture was boiled then was cooled at −10° C. to yield precipitate. The precipitate was collected, washed with 50 ml of cold acetonitrile and air dried. The material was recrystallized from 150 ml of boiling acetonitrile after treatment with activated charcoal and filtration by cooling at −10° C. The product of the Example was collected by filtration, washed with 50 ml of cold acetonitrile and dried to give 4.0 g of a tan solid, mp 181°–183° C.

EXAMPLE 25

1-[5-Methyl-2-(4-pyridinyl)-1H-imidazol-4-yl]-ethanone oxime

To a 1.0 g (0.005 mole) amount of 1-[5-methyl-2-(4-pyridinyl)-1H-imidazol-4-yl]ethanone (prepared as described in Example 24) dissolved in 200 ml of boiling water were added 1.0 g (0.012 mole) of sodium acetate and 0.7 g (0.01 mole) of hydroxylamine hydrochloride. The mixture was stirred and heated for 2 hours, then cooled to room temperature. The resulting precipitate was collected by filtration and when dried at 60° C. for 18 hours gave 0.7 g of the product of the Example as white crystals, mp 253°–255° C. (dec.).

EXAMPLE 26

1-[2-(6-Chloro-3-pyridinyl)-5-methyl-1H-imidazol-4-yl]ethanone

A mixture of 4.5 g (0.035 mole) of 2,3,4-pentanetrione 3-oxime and 5.3 g (0.037 mole) of 6-chloro-3-pyridylmethylamine in 100 ml of acetonitrile was stirred at the reflux temperature for 18 hours. The reacted mixture was cooled at −10° C. with formation of a precipitate. The precipitate was washed, dried and recrystallized as for Example 24 to give 2.6 g of the desired product as a pale yellow solid, mp 239°–240° C.

EXAMPLE 27

1-[5-Methyl-2-(3-methyl-4-pyridinyl)-1H-imidazol-4-yl]ethanone

A mixture consisting of 7.1 g (0.058 mole) of 3-methyl-4-pyridylmethylamine, 6.25 g (0.051 mole) of 2,3,4-pentanetrione 3-oxime, and 125 ml of acetonitrile was stirred at the reflux temperature for four hours. After cooling at −10° C., a precipitate formed. This was collected, washed with a little cold acetonitrile, and dried. Recrystallization from a mixture of chloroform and hexane gave 4.5 g of the desired product, mp 185°–187° C.

EXAMPLE 28

1-[5-Methyl-2-(3-methyl-4-pyridinyl)-1H-imidazol-4-yl]ethanone oxime hydrate

To a 1.0 g (0.005 mole) amount of 1-[5-methyl-2-(3-methyl-4-pyridinyl)-1H-imidazol-4-yl]ethanone (prepared as described in Example 27) dissolved in 200 ml of boiling water, were added 1.0 g (0.012 mole) of sodium acetate and 0.7 g (0.01 mole) of hydroxylamine hydrochloride. The mixture was stirred and heated for 3 hours, then cooled at room temperature. The resulting precipitate was collected by filtration and when dried at 60° C. for 18 hours gave 0.6 g of the desired product as its hydrate, a yellowish powder, mp 195°–197° C. (dec.).

We claim:

1. A compound selected from the group consisting of those of the formula:

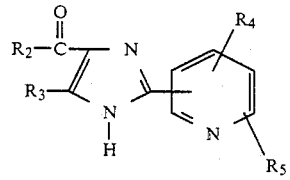

wherein $R_2$ is alkyl($C_1$–$C_5$), cycloalkyl($C_3$–$C_6$) or phenyl, $R_3$ is alkyl($C_1$–$C_3$), and $R_4$ and $R_5$ are each hydrogen, chloro or methyl with the proviso that $R_4$ and $R_5$ may not be dichloro or dimethyl; the oxime thereof; the methoxime thereof; the semicarbazone thereof; the pyridine-1-oxide thereof; the 1-alkylpyridinium halide thereof; the 1-(phenylalkyl)-pyridinium halide thereof; the tautomer thereof; and the pharmacologically acceptable acid-addition salts thereof.

2. The compound according to claim 1; 1-[5-methyl-2-(3-pyridinyl)-1H-imidazol-4-yl]-1-ethanone.

3. The compound according to claim 1; [5-methyl-2-(3-pyridinyl)-1H-imidazol-4-yl]phenylmethanone.

4. The compound according to claim 1; 1-[5-propyl-2-(3-pyridinyl)-1H-imidazol-4-yl]-1-butanone.

5. The compound according to claim 1; 1-[5-methyl-2-(3-pyridinyl)-1H-imidazol-4-yl]-2-methyl-1-propanone.

6. The compound according to claim 1; 1-[5-methyl-2-(3-pyridinyl)-1H-imidazol-4-yl]-1-butanone.

7. The compound according to claim 1; 1-[5-methyl-2-(3-pyridinyl)-1H-imidazol-4-yl]-1-pentanone.

8. The compound according to claim 1; 1-[5-methyl-2-(3-pyridinyl)-1H-imidazol-4-yl]-2,2-dimethyl-1-propanone.

9. The compound according to claim 1; 1-[5-methyl-2-(3-pyridinyl)-1H-imidazol-4-yl]-1-hexanone.

10. The compound according to claim 1; 1-[5-methyl-2-(3-pyridinyl)-1H-imidazol-4-yl]-1-propanone.

11. The compound according to claim 1; 1-[5-methyl-2-(3-pyridinyl)-1H-imidazol-4-yl]-3-methyl-1-butanone.

12. The compound according to claim 1; 1-[5-ethyl-2-(3-pyridinyl)-1H-imidazol-4-yl]-1-propanone.

13. The compound according to claim 1; 1-[5-methyl-2-(3-pyridinyl)-1H-imidazol-4-yl]-2-methyl-1-butanone.

14. The compound according to claim 1; [5-methyl-2-(3-pyridinyl)-1H-imidazol-4-yl]cylcopropylmethanone.

15. The compound according to claim 1; [5-methyl-2-(3-pyridinyl)-1H-imidazol-4-yl]cyclohexylmethanone.

16. The compound according to claim 1; 1-[5-ethyl-2-(3-pyridinyl)-1H-imidazol-4-yl]-2,2-dimethyl-1-propanone.

17. The compound according to claim 1; 1-[5-methyl-2-(2-pyridinyl)-1H-imidazol-4-yl]-1-ethanone.

18. The compound according to claim 1; 1-[2-(2-chloro-6-methyl-3-pyridinyl)-5-methyl-1H-imidazol-4-yl]-1-ethanone.

19. The compound according to claim 1; 1-[5-methyl-2-(4-pyridinyl)-1H-imidazol-4-yl]-1-ethanone.

20. The compound according to claim 1, 1-[2-(6-chloro-3-pyridinyl)-5-methyl-1H-imidazol-4-yl]-1-ethanone.

21. The compound according to claim 1; 1-[5-methyl-2-(3-pyridinyl)-1H-imidazol-4-yl]-1-ethanone oxime.

22. The compound according to claim 1; 1-[5-methyl-2-(4-pyridinyl)-1H-imidazol-4-yl]-1-ethanone oxime.

23. The compound according to claim 1; 1-[5-methyl-2-(3-methyl-4-pyridinyl)-1H-imidazol-4-yl]-1-ethanone oxime.

24. The compound according to claim 1; 1-[5-methyl-2-(3-pyridinyl)-1H-imidazol-4-yl]-1-ethanone methoxime.

25. The method of lowering elevated blood pressure in a mammal which comprises administering internally to said mammal a hypotensive effective amount of a compound of claim 1.

* * * * *